United States Patent [19]
Vierling et al.

[11] Patent Number: 5,914,228
[45] Date of Patent: Jun. 22, 1999

[54] DIRECT DETECTION OF HEPATITIS C VIRUS RNA

[75] Inventors: John M. Vierling, Beverly Hills; Ke-Qin Hu, Los Angeles, both of Calif.

[73] Assignee: Cedars-Sinai Medical Center, Los Angeles, Calif.

[21] Appl. No.: 08/335,595

[22] Filed: Nov. 8, 1994

Related U.S. Application Data

[63] Continuation of application No. 08/175,473, Dec. 23, 1993, abandoned, which is a continuation of application No. 07/758,862, Sep. 12, 1991, abandoned.

[51] Int. Cl.⁶ .............................. C12Q 1/70; C12Q 1/68; C12P 19/34; C07H 21/04
[52] U.S. Cl. .................................. 435/5; 435/6; 435/91.1; 435/91.2; 536/23.1; 536/24.3; 536/24.32; 536/24.33
[58] Field of Search ........................... 435/6, 5, 91, 91.2; 536/24.2, 23.1, 24.32, 24.33, 26.6

[56] References Cited

U.S. PATENT DOCUMENTS

| | | | |
|---|---|---|---|
| 5,124,246 | 6/1992 | Urdea et al. | 435/6 |
| 5,350,671 | 9/1994 | Houghton et al. | 435/5 |
| 5,372,928 | 12/1994 | Miyamura | 435/5 |

OTHER PUBLICATIONS

Houghton, Michael et al., "Molecular Biology of the Hepatitis C Viruses: Implications for Diagnosis, Development and Control of Viral Disease," Hepatology, 14:381–388 (Aug. 1991).
Choo et al. Science 244:359–362, 1989.
Okamoto et al Japan J. Exp. Med vol. 60(3) pp. 167–177 issued Feb. 1990.
Takeuchi et al. J. of Gen. Virology vol. 71 pp. 3027–3033 issued Dec. 1990.
Kato et al. Proc. Natl. Acad. Sci USA vol. 87 pp. 9524–9528 issued Dec. 1990.

*Primary Examiner*—W. Gary Jones
*Assistant Examiner*—Dianne Rees
*Attorney, Agent, or Firm*—Lyon & Lyon LLP

[57] ABSTRACT

The methods and compositions of this invention provide a fast, accurate means for directly determining the presence and quantity of HCV in a sample, and thus in a patient, through hybridization to patient samples using a probe specific for HCV. They allow detection of both acute and chronic HCV infection. These methods and compositions also allow for the effective monitoring of therapeutic procedures for treating HCV infection.

95 Claims, 5 Drawing Sheets

FIG. 1.

HCV ORF (9033 nt TRANSLATE 3011 AA)

C=CORE; E=ENVELOPE; NS=NON-STRUCTURE; ORF=OPEN READING FRAME; nt=NUCLEOTIDE; AA=AMINO ACID; kb=KILOBASE PAIR

FIG. 2.

5'-ACTCCACCATAGATCATCCC-3'   (7-26 nt, sense)

5'-AACACTACTCGGCTAGCAGT-3'   (229-248 nt, anti-sense)

```
         *         *         *         *         *         *  50
(1) ......ACTCCACCATAGATCACTCCCCTGTGAGGAACTACTGTCTTCACG
(2)    ------------GA--------------------------------------

*         *         *         *         *         * 100
    CAGAAAGCGTCTAGCCATGGCGTTAGTTAGAGTGTCGTGCAGCCTCCAGG
    --------------------------------------------------

*         *         *         *         *         * 150
    ACCCCCCCTCCCGGGAGAGCCATAGTGGTCTGCGGAACCGGTGAGTACACC
    --------------------------------------------------

*         *         *         *         *         * 200
    GGAATTGCCAGGACGACCGGGTCCTTTCTTGGATAAACCCGCTCAATGCC
    --------------------------------------------C-----

*         *         *         *         *         * 250
    TCGAGATTTGGGCGCGCCCCCGCAAGACTGCTAGCCGAGTAGTGTT..........
    -----------------T------------------------------ .......
```

DIRECT DETECTION OF HEPATITIS C VIRUS RNA

This is a continuation of application Ser. No. 08/175,473, filed Dec. 23, 1993, abandoned, which is a continuation of Ser. No. 07/758,862, filed Sep. 12, 1991, abandoned.

BACKGROUND OF THE INVENTION

Five unique human hepatitis viruses have been identified (1–5). The hepatitis A virus and hepatitis E virus are enterically transmitted RNA viruses that do not cause chronic liver disease. In contrast, the hepatitis B virus, hepatitis C virus and hepatitis D virus (HBV, HCV and HDV, respectively) are parenterally transmitted and cause chronic infection. They are dangerous contaminants of the blood supply. Recently tests have become readily available for testing for HBV in blood, allowing for the screening for this pathogen and the elimination of infected samples from the blood supply (6).

Concomitant with the availability of the HBV test came an increase in the proportion of cases of post-transfusion hepatitis due to non-A, non-B (NANB) agents. Until recently, there was no test available for the detection of the NANB agents. The principal NANB agent, HCV, was recently identified by molecular cloning of segments of the HCV genome (3). HCV is an RNA virus related to human flaviviruses and animal pestiviruses (7,8).

Prospective studies of selected counties in the United States by the Centers for Disease Control (CDC) indicate that approximately 170,000 new cases of NANB/HCV infection occur yearly (9). At least 50% of these infections appear to progress to chronic liver disease. Severe sequelae include the development of decompensated cirrhosis necessitating liver transplantation, and development of hepatocellular carcinoma (10,11).

The positive-stranded RNA genome of the HCV contains approximately 10,000 nucleotides. The HCV genome acts as a long open reading frame (ORF) capable of encoding a 3,010 amino acid polyprotein precursor from which individual viral proteins, both structural and nonstructural, are produced (7,12–14). There are at least 324 nucleotides at the 5'-end of the ORF which have not yet been shown to encode for protein. Thus, this sequence is referred to as the 5'-non-coding region (7,12–17). Several research groups have reported the nucleotide sequence of either the whole HCV genome or specific subgenomic regions (7,12–22). Comparison of these sequences demonstrates variations in the structural and nonstructural regions (ranging from 9–26%) among different HCV strains. In contrast, the sequences of the 5'-non-coding region appear to have a homology of approximately 99% among different strains (16,17). The 5'-non-coding region also has substantial homology (45–49%) with the equivalent region of animal pestiviruses (7).

Two major techniques are currently used to detect HCV infection. The first technique detects antibody produced in response to HCV infection (anti-HCV) (23–28). Since multiple weeks are required for infected patients to develop detectable IgG antibody against HCV antigens, this test is useless in the detection of acute HCV infection. Moreover, studies indicate that antibody testing is associated with both false positive and false negative results (29).

These shortcomings in the original assays have spurred development of newer supplemental antibody tests for the diagnosis of HCV infection (30). Preliminary results with supplemental assays indicate a decrease in the frequency of false-positive and negative results. However, false-positive and -negative results still occur and supplemental tests remain unsuitable for detection of acute infection (31).

The second technique, detection of HCV RNA by an RNA polymerase chain reaction (PCR), has been limited to research use. The HCV PCR evaluates infection by detecting HCV RNA in blood or tissue extracts through reverse transcription and cDNA amplification (7,32–41). HCV PCR represents a sensitive, direct technique but requires meticulous care (7) to prevent false positive and negative results. The HCV PCR technique, in contrast to antibody tests, can detect circulating HCV RNA during acute infection.

The original HCV PCR tests used primers specific for sequences in the non-structural region of the HCV genome (32–36). Subsequently, HCV PCR has been performed using several primers for the 5'-non-coding region in the genome (37,39). In our laboratory we have established HCV PCR for both the nonstructural and 5'-non- coding regions. Our comparative results indicate that the HCV PCR from the 5'-non-coding region is more sensitive in detecting HCV infection (41).

Despite the success of HCV PCR, the technique has many inherent limitations. First, it is time consuming, expensive and dependent upon meticulous technique. The exquisite sensitivity of PCR makes false positive results due to contamination with exogenous HCV RNA a constant concern (42). Moreover, the variation in both the reverse transcription of HCV RNA to CDNA and the amplification of cDNA make the HCV PCR difficult to quantitate (38,40, 42). Recent attempts to overcome these obstacles have resulted in, at best, semi-quantitative assays (38). More importantly, in our experience the efficiency of HCV PCR depends in large part on the specific primers employed. Not only have standards for primers not been developed, but polymerases employed in PCR have different efficiencies. Thus, it will likely be difficult to compare PCR results among different laboratories.

To overcome the limitations of current antibody and HCV PCR techniques for detection of HCV infection, it is desirable to develop a test which is highly sensitive, specific, affordable and applicable to the testing of large populations of patients or blood donors. The optimal test would be capable of detecting both acute and chronic infection. Moreover, it would be quantitative to provide information regarding both natural history and the efficacy of current or future antiviral therapies. It would be capable of uniform results. These prerequisites can be fulfilled by a technique to directly detect HCV RNA.

SUMMARY OF THE INVENTION

The methods and compositions of this invention provide a fast, accurate means for directly determining the presence and quantity of HCV in a sample, and thus in a patient, through hybridization to patient samples using a probe specific for HCV.

Further, the methods and compositions of this invention provide a means of detecting both acute and chronic HCV infection.

The methods and compositions herein described allow for a quantitative analysis of HCV presence and infection. They provide a means for uniformity of results previously unavailable.

Additionally, these methods and compositions are highly sensitive, and specific to the HCV virus.

These methods and compositions are both rapid and economical, making them suitable for screening of large populations. They provide quick results which can aid in the treatment of infected subjects. They also allow for rapid and economical screening of blood supplies for contamination by HCV.

In addition to the obvious importance in differential diagnosis of liver disease and screening of donated blood, direct detection of HCV RNA facilitates studies of the pathogenesis of HCV infection. Specifically, these methods can be used, among other things, to: 1) quantitate precisely the amount of circulating HCV; 2) analyze the molecular forms of HCV RNA during the evolution of disease; 3) localize HCV in hepatic and/or extrahepatic tissues; and 4) study the relationship between HCV infection, hepatocellular necrosis and hepatocellular carcinoma.

These methods and compositions also allow for the effective monitoring of therapeutic procedures for treating HCV infection.

BRIEF DESCRIPTION OF THE DRAWINGS

The present invention may be better understood and its advantages appreciated by those skilled in the art by referring to the accompanying drawings wherein.

DESCRIPTION OF THE INVENTION

The present invention provides methods and compositions for detecting HCV through the use of RNA slot blots and the specific probes identified herein.

RNA slot hybridization represents a classic technique for detection of RNA through hybridization to specific nucleotide probes labeled with either radioisotopes or nonradioactive materials such as fluorescent or enzyme linked labels. This technique has yielded excellent sensitivity in the detection of other viral infections (43). However, original data on HCV indicated that the titer of circulating virus would be too low to be detected by direct hybridization methods (3). In the original publication of the molecular cloning of HCV, a $^{32}$P-labeled nonstructural HCV cDNA was used to demonstrate the specificity of cloned HCV cDNA (3). The published Northern blots were hybridizations between the cDNA probe and poly (A)+RNA from the liver of an infected chimpanzee. Subsequent studies of RNA hybridization of blood or tissue have not been reported, and recent reports (7,47) argue that quantities of HCV RNA found in infected samples are insufficient for detection through direct hybridization.

Figure 1:
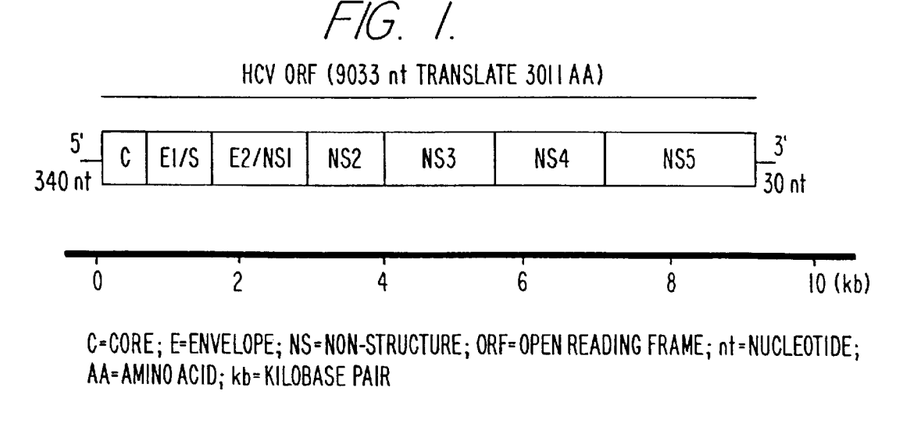
FIG. 1 shows the general structure of the HCV genome as described in reference 7 and 13.

Based on our own results (41), and those published in the literature (7,16,17), indicating that the 5'-non-coding region of the HCV genome is more highly conserved than either the structural or nonstructural regions, we have performed extensive analysis of HCV PCR using primers specific for this region. As indicated above, the HCV PCR in the 5'-non-coding region is more sensitive than HCV PCR using primers specific for either the NS3 or NS4 regions (see FIG. 1 for location of these regions) (7,13). Based on these results, we developed a series of 5'-non-coding region probes to detect circulating HCV RNA using RNA slot hybridization (44).

Additionally, these probes are useful for detection of HCV RNA through Northern blots, in situ hybridization of tissues, as well as for priming PCR.

DEFINITIONS 5'-non-coding region of HCV nucleotides refers to the entire nucleotide sequence of all HCV strains located upstream (5'-end) of the initial codon of the large HCV ORF. This includes the 241 base pair sequence from nucleotide 7 to nucleotide 248 of the HCV sequence numbered according to the system of Okamoto et al. (16).

Probe refers to a defined nucleotide sequence, such as cDNA or RNA, of any length that is labeled. Any labeling method known in the art can be used, such as radioisotopes, FITC or other fluorochrome markers, enzymes, biotin, digoxigenin, or other molecules capable of secondary detection.

Detection refers to any technique known in the art in which probes may be used to detect the presence of HCV RNA, including but not limited to dot blot hybridization, slot blot hybridization, Northern blot or in situ hybridization.

Samples refers to clinical materials, including but not limited to blood, secretions, tissues, or organs from HCV infected patients and animals, and cell lines containing HCV whole genomes or subgenomic elements induced by infection, injection, transfection, transformation, lipofection, electroporation, or other means known in the art for transferring nucleic acid into or onto cells, or production of hybridomas.

SELECTION OF PROBES

This invention provides probes for detection of HCV. The 5'-non-coding region is identified herein as the source of useful probes for the detection of HCV. Probes were cloned from the 5'-non-coding region of the HCV genome and tested for their homology to HCV and their specificity to that virus. Any of numerous techniques well known in the art can be used for this purpose. (46) DNA probes can be made from viral RNA by using a variety of techniques, including but not limited to conventional cDNA cloning, and reverse transcription-PCR, such as by using a GeneAmp RNA PCR Kit (Perkins Elmer Cetus, Norwalk, Conn.). When reverse transcription-PCR is used, a specific PCR product is then identified by agarose electrophoresis, ethidium bromide staining and Southern blot hybridization using labeled primers as the probe.

Selected cDNAs are then amplified for later use as probes. Examples of methods for this amplification are PCR, synthesis of riboprobes, and cellular amplification of cDNA clones. Construction of such clones is by standard procedures. Cleavage is performed by treating with restriction enzyme(s) in suitable buffers. Contaminating protein can be removed by a variety of methods such as phenol/chloroform extraction. (46) The cDNA is prepared for insertion into suitable vectors using appropriate techniques, such as blunt ending, via single strand exonucleases or fill in repair, or addition of linkers where necessary to facilitate ligation. Additionally, inserts can be dephosphorylated or phosphorylated where appropriate to aid in the insertion of the appropriate number of copies into the vector.

Vectors can be selected for a number of characteristics such as their ease of amplification and their ability to incorporate the appropriate size insert. Ligation and amplification are by standard techniques known in the art. (46)

After amplification of the probe sequence, the probes are separated from their amplification means, such as by cleavage and purification from the amplification vectors, or by purification from the PCR preparation or riboprobe preparation.

Sensitivity of the probe is increased when only the antisense portion is used. If such an increase in sensitivity is desired, the antisense strands can be separated from the sense strands by a variety of means. Alternatively, when using probes such as riboprobes, the antisense strand alone can be amplified, obviating the need to remove any sense strands.

The probe is labelled by any standard technique known in the art, such as radiolabelling, fluorescence, and enzyme linked immunoassays.

The probes of this invention contain at least one contiguous stretch of sequence in the 5'-non-coding region of the HCV genome sufficiently long to allow hybridization to HCV RNA or cDNA in the sample. A preferred probe sequence contains at least 20 contiguous nucleotides from the sequence shown in FIG. 4 (SEQ ID NO:1). Current evidence shows that an oligonucleotide of as few as six nucleotides is sufficient for hybridization (48). Additionally, probes from the 5'-non-coding region can be mixed with sequences from other regions of the HCV genome, such as structural or other non-structural regions, to enhance sensitivity. Probes are constructed so that non-homologous regions of the probes do not interfere with hybridization by the homologous region(s). Non-homologous regions cannot be homologous with other DNA or RNA sequences which might also be contained in the sample due to contamination or presence in the cell's genome. Additionally, non-homologous regions cannot be so long that they prevent hybridization by the homologous regions by physically interfering with that hybridization to the HCV nucleic acid in the sample.

SAMPLE PREPARATION

For detection of the presence of HCV, samples of serum or other fluids or tissues from patients can be readily prepared for hybridization with the probes of this invention. Viral RNA is isolated from volumes of patient serum samples from as little as 0.4–0.5 mls according to standard procedures. Methods of RNA purification using guanidinium isothiocyanate have proven to be especially useful in providing sufficient RNA from patient samples. (45,46)

HYBRIDIZATION

The probes identified above can be used in a number of procedures for the easy detection of HCV. Slot hybridization provides an especially simple and quick procedure for this detection. Techniques for slot hybridization are well known in the art, and are described in a variety of publications, such as reference 41. Additionally, the probes of this invention can be used for Northern bot hybridization, in situ hybridization of tissues, as well as for priming PCR.

QUANTIFICATION

The amount of HCV present in a sample can be measured using the intensity of label bound as compared to a series of standards. HCV is generally measured in Chimpanzee Infectious Doses, or CIDs (49). A range of dilutions of HCV RNA can be used as standards against which the results of slot blot hybridization analysis of a sample can be compared.

The ability to quantify HCV facilitates analysis of the natural history of the untreated disease. Additionally, quantification allows monitoring of the therapeutic potential of currently used as well as potential new therapeutic regimens.

DIAGNOSTIC TESTS

The probes and methods of this invention can be packaged in a form amenable to diagnostic testing for the presence of HCV in patient samples. For example, a slot blot kit can be supplied with means for analyzing samples, including means for preparation of samples including purification of RNA and serial dilutions, labelled probes, hybridization solutions, as well as standards for quantitative comparison.

Such test kits can be used for diagnosis of infection by HCV. Due to the quantitative nature of the test kits, they can be used as well for monitoring the progress of the infection and evaluation of anti-viral therapies administered to the patient or being tested in vitro. Currently, evaluation of pathogenesis and anti-viral therapies for infection by HBV can be studied in tissue culture through transfection of the cells by HBV (50). Comparable tissue culture systems, as well as animal models, may become available for the study of HCV. The methods and probes of this invention will allow quick and efficient monitoring of HCV pathogenesis and susceptibility to drug therapies in these in vitro and animal model systems as well as in humans.

Additionally, test kits can be used by blood banks to screen blood samples for contamination by HCV. This direct HCV RNA testing to detect acute or chronic infection is superior to antibody screening due to its superior accuracy and sensitivity. Therefore, the techniques of this invention will permit substantial reduction in the risk of post-transfusion HCV infection and eliminate the current need to discard donated blood with false-positive anti-HCV tests.

Similarly, the above diagnostic and monitoring activities can be performed using the methods and probes of this invention in an unpackaged form. The procedures described herein for preparation of probes, preparation of samples, hybridization of probes to samples, and detection and quantification of hybridization are standard and readily available to one of reasonable skill in the art. Therefore, from the teachings of this invention, such an artisan will be enabled to gather the appropriate supplies and perform the necessary steps to detect HCV RNA according to this invention.

The following examples are provided by way of illustration to further assist in the understanding of this invention.

EXAMPLE 1

Development of Probes

Figure 2:
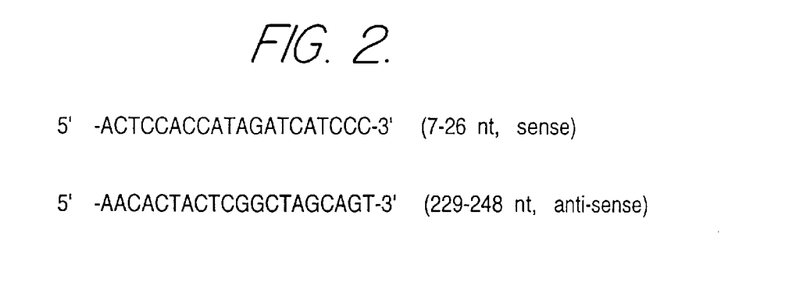
FIG. 2 shows the oligonucleotide sequences of primers used in the examples for HCV PCR.

To obtain HCV cDNA nucleotide sequences from the 5'-non-coding region, we used a pair of oligonucleotides (FIG. 2) as primers for HCV PCR according to the sequences of HC-J1 reported by Okamoto et al. (16). HCV RNA was isolated from 0.4 ml of a serum sample from a putatively HCV infected individual using the guanidinium isothiocyanate-acid-phenol technique (45). RNA reverse transcription-PCR was performed using a GeneAmp RNA PCR Kit (Perkins Elmer Cetus, Norwalk, Conn.). A specific PCR product was identified by agarose electrophoresis, ethidium bromide staining and Southern blot hybridization using $^{32}$P-labeled primers (FIG. 2) as the probe.

Figure 3:
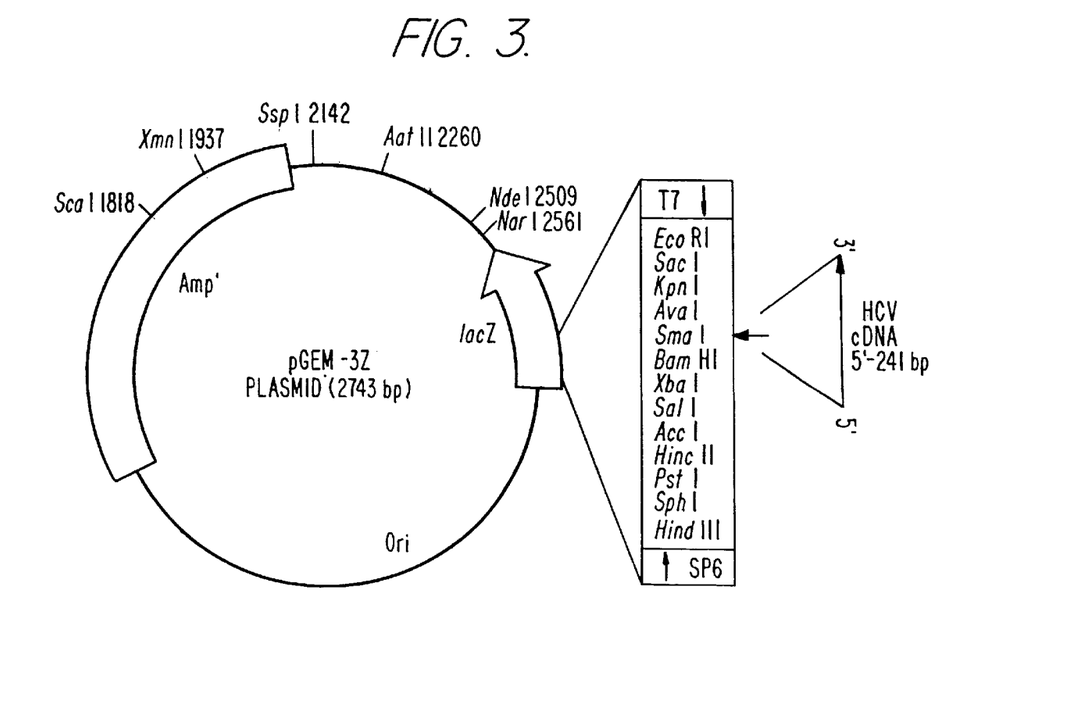
FIG. 3 presents the structure of plasmid pGHCV1A.

After determining the specificity of the PCR product by Southern blot analysis using the PCR primers, the product was purified and blunted using T4 DNA polymerase according to standard methods (46). The fragment was then cloned into Smal I site of pGEM-3Z, a plasmid vector (Promega Co., Madison, Wis.). An E.coli cell line, DH5α, (GIBCO/BRL Inc., Gaithersberg, Md.) was transformed with cloned DNA. Positive clones then were screened by restriction digestion and $^{32}$P-labeled oligonucleotides. FIG. 3 shows the structure of pGHCV1A, which contains a 241 base pair insertion from the HCV 5'-non-coding region.

Figure 4:
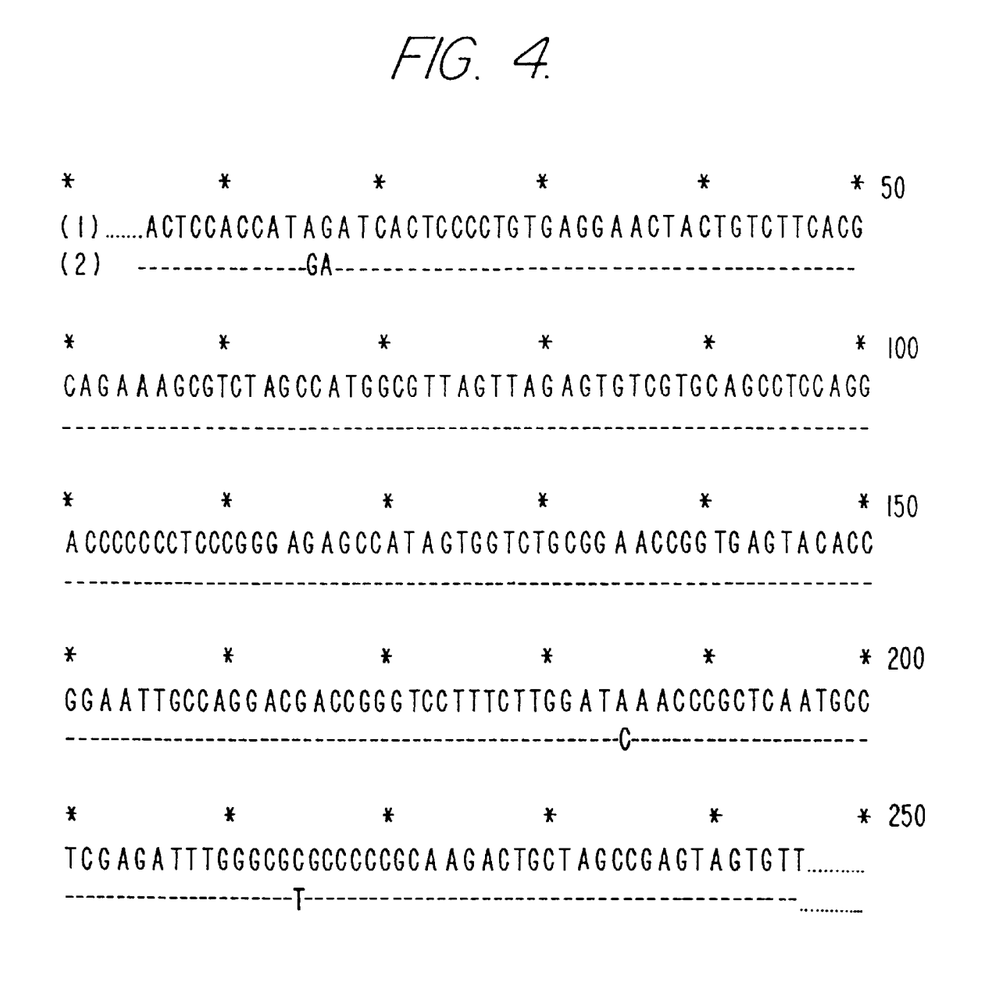
FIG. 4 shows the cDNA sequences of cloned HCV 5'-non-coding region in pGHCV1A.

DNA sequencing was then performed to determine the specificity of cloned HCV sequence in pGHCV1A. The sequencing kit was obtained from USB Co., Cleveland, Ohio and the SP6 and T7 primers were purchased from Promega, Co. As shown in FIG. 4, pGHCV1A contains a 241 base pair sequence of the HCV 5'-non-coding region, which is 100% homologous with the sequence of the HC-J1 strain reported by Okamato et al. (16). As shown in FIG. 4, four nucleotides differ between the HC-J1 strain and the HCV-I strain reported by the Houghton group (12,14). The orientation of our cloned HCV sequence is shown in FIG. 3.

To obtain a HCV cDNA probe, the cloned HCV fragment was purified by simultaneous restriction digestion with Bam HI and Kpn I and glass powder elution (46). The purified HCV fragment was labeled with $^{32}$P-dCTP by nick translation or by a random primer DNA labeling kit (BIO-RAD Lab, Richmond, Calif.). RNA probes (riboprobes) were synthesized in vitro from the HCV cDNA template present in pGHCV1A by both SP6 or T7 RNA polymerase reactions (Boehinger Mannheim Co., Indianapolis, Ind.). Riboprobes were labeled by incorporation of $^{32}$P-UTP. SP6 RNA polymerase synthesizes a HCV riboprobe with sense orientation, whereas, T7 RNA polymerase synthesizes a HCV riboprobe with anti-sense orientation (See FIG. 3).

EXAMPLE 2

Slot Hybridization of HCV RNA

METHODS

RNA-CDNA Hybridization. 1) RNA Extraction: A 0.4 ml aliquot of serum was clarified and RNA extracted using the guanidinium isothiocyanate-acid-phenol technique (45). 2) Slot Blot: A standard method (46) was used. Nytran nylon membrane (Schleicher & Schuell Inc., Keene, N.H.) was used for blotting tested samples. 3) Probes: The procedures for making $^{32}$P-labeled HCV probes have been described above in Example 1. Probes were further purified by Sephadex G50 column chromatography (46). 4) Prehybridization and Hybridization: Blotted membranes were prehybridized at 65° C. for 3 to 4 hours and then hybridized with $^{32}$P-labeled HCV probes (46) at 65° C. for 20 to 24 hours. 5) Autoradiography: After washing, the membranes were exposed to x-ray film (Kodak, Rochester, N.Y.) at −70° C. for 24 to 48 hours.

RNA-RNA Hybridization. The procedure was similar to RNA-cDNA hybridization except that riboprobes were used instead of cDNA probes. After labeling, riboprobes were purified by DNase digestion and Sephadex G50 column chromatography (46).

RESULTS

Figure 5:
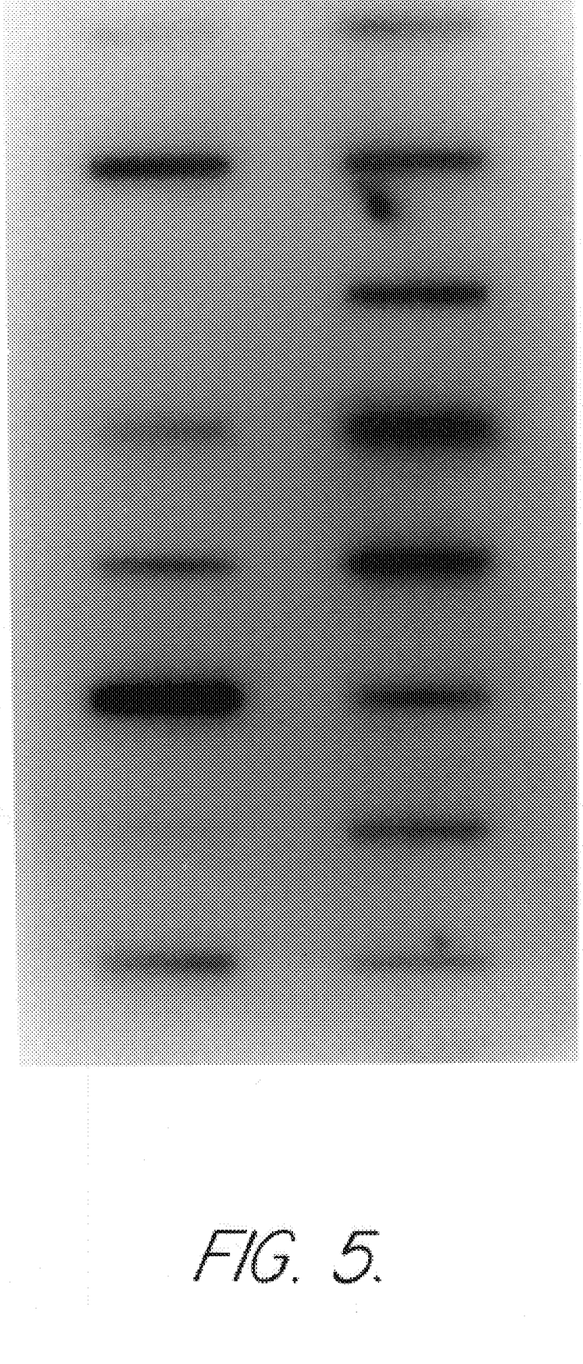
FIG. 5 shows a sample slot hybridization on various patient samples.
Figure 6:
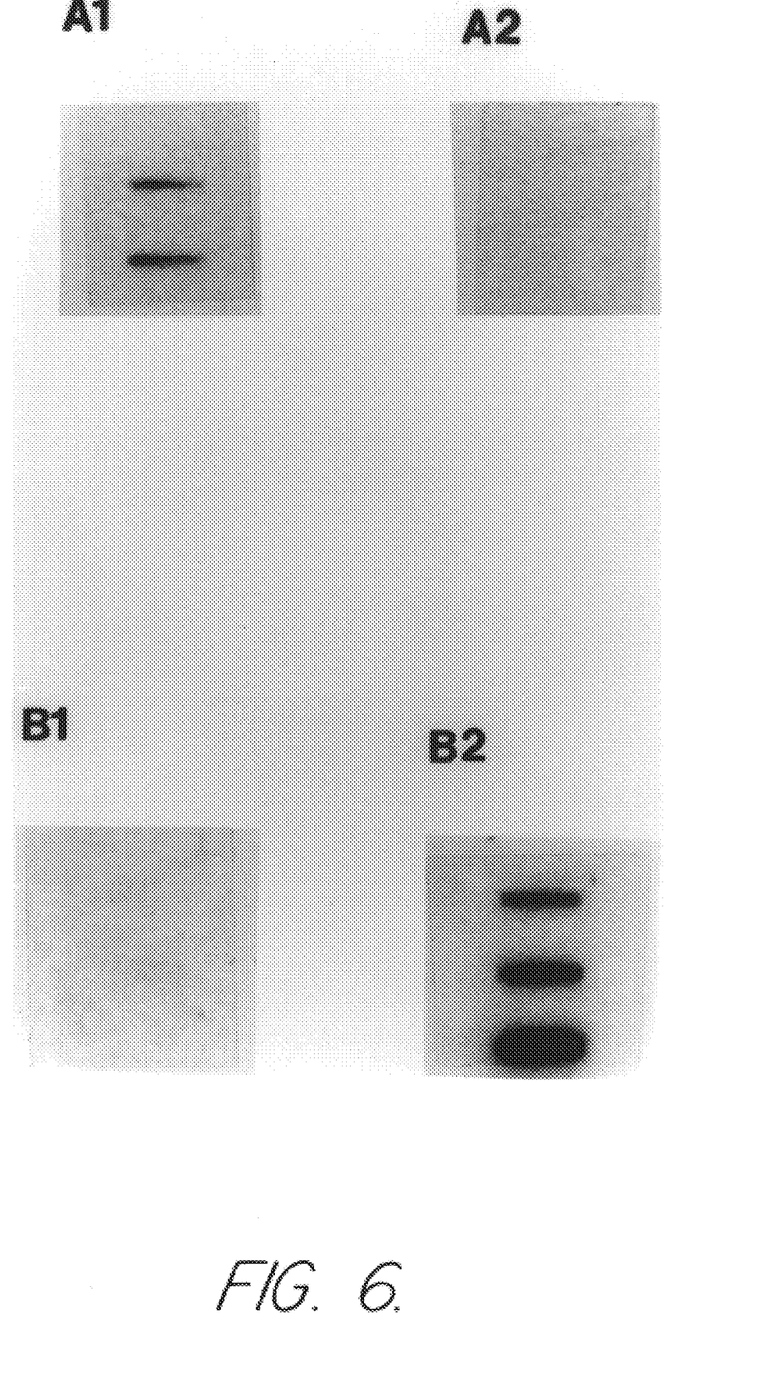
FIG. 6 shows assays for specificity of slot hybridization.
Figure 7:
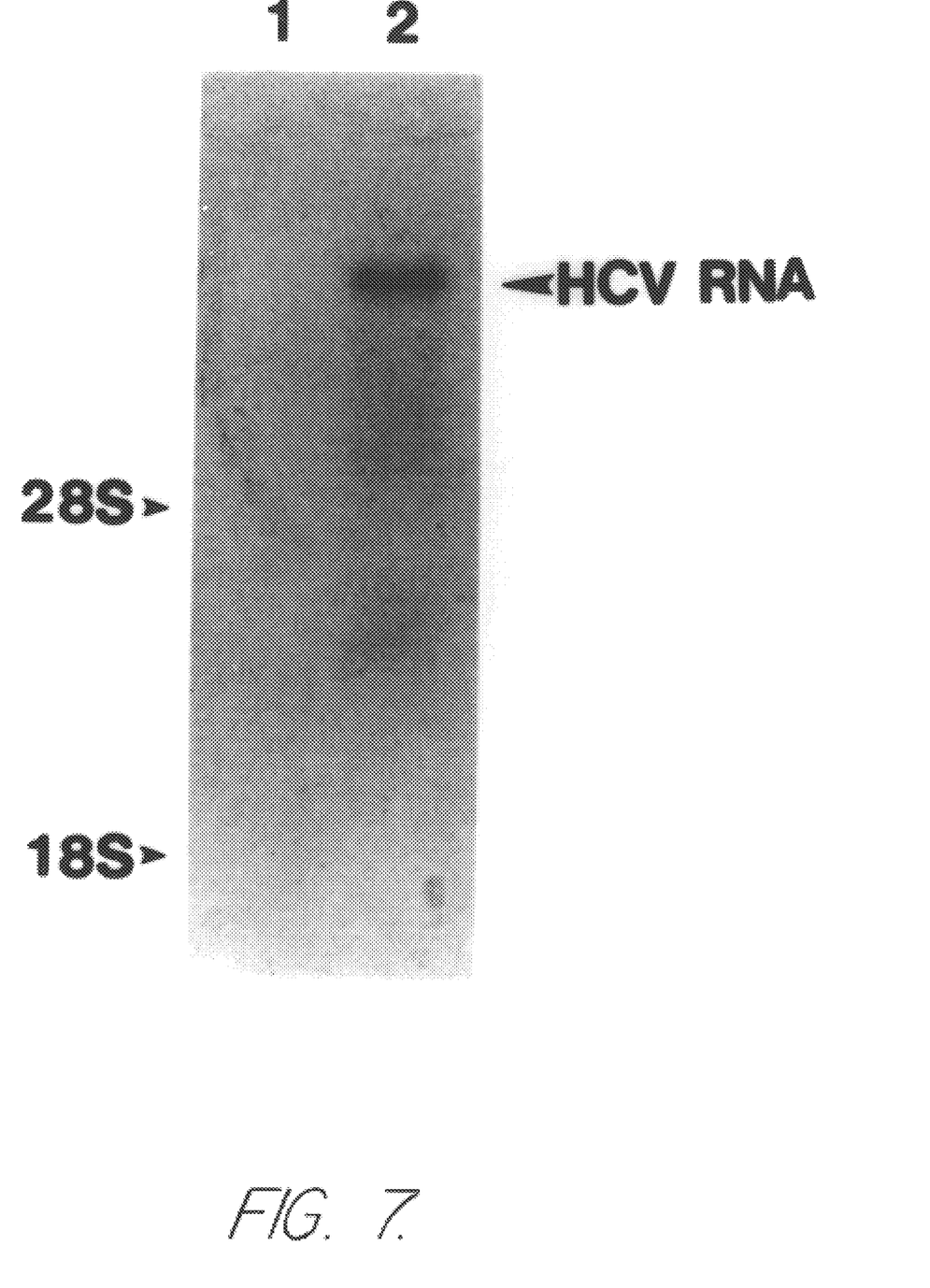
FIG. 7 presents a Northern blot of HCV RNA.

Specificity: As shown in FIG. 5, RNA-CDNA slot hybridization produced ideal results. The specificity was determined by the following tests: 1) the probe was sequenced to verify its homology with published HCV sequences (FIG. 4); 2) normal human AB serum and normal horse serum were used as the negative controls; neither hybridized with the HCV probes; 3) a concordance of 96% was observed between RNA slot hybridization and HCV PCR using primers for the 5'-non-coding region (Table 1); 4) hybridization signals (FIG. 6 A1) were abolished by pretreatment of viral RNA with RNase A at 37° C. for 30 minutes (FIG. 6 A2); 5) using riboprobes, only the anti-sense riboprobe synthesized from T7 RNA polymerase produced a hybridization signal (FIGS. 6 B1, B2); and 6) Northern blot assays showed that our probe hybridizes with HCV-infected serum samples to produce a signal band of approximately 10 kb (FIG. 7). Our combined data indicate that our slot hybridization technique is very specific for HCV RNA. Moreover, compared with HCV PCR, our slot hybridization did not show any false positive reactions with serum samples from patients without HCV infection (Table 1).

TABLE 1

Concordance of HCV PCR and Slot Hybridization

|  | HCV PCR (+) | HCV PCR (−) |
| --- | --- | --- |
| HCV-RNA-cDNA Hybr(+) | 48 | 0 |
| HCV-RNA-cDNA Hybr(−) | 2 | 10 |

Sensitivity: High sensitivity was indicated by a concordance of 96% between the slot hybridization and HCV PCR and the absence of false positive results (Table 1). When compared with the probes from NS4 (34), the 5'-non-coding region probe was much more sensitive (Table 2). The sensitivity is evaluated by HCV-infected chimpanzee blood sample with known quantitated infectious units of HCV (gift of H. Alter, M.D., NIH, Bethesda, Md.). Use of an anti-sense riboprobe for RNA-RNA hybridization shows greater sensitivity than does the cDNA probe (Table 2).

TABLE 2

Comparison of HCV RNA Testing Using Different Assays

| | | Slot Hybridization Assays | | |
| --- | --- | --- | --- | --- |
| n = 30 | HCV PCR | 5'-cDNA | 5'-riboprobe | NS4-cDNA |
| Positive | 25 | 23 | 25 | 14 |
| Negative | 5 | 7 | 5 | 16 |

While the preferred embodiments have been described and illustrated, various substitutions and modifications may be made thereto without departing from the scope of the invention. Accordingly, it is to be understood that the present invention has been described by way of illustration and not limitation.

References

1. Cohen J. I. Hepatitis A virus: insights from molecular biology. hepatology 1989; 9:889–895.
2. Ganem D. and Varmus H. E. The molecular biology of the hepatitis B viruses. Ann. Rev. Biochem. 1987; 55:651–693.
3. Choo Q. L., Kuo G,. Weiner A. J., et al. Isolation of a CDNA clone derived from a blood-borne non-A, non-B viral hepatitis genome. Science 1989; 244:359–362.
4. Hoofnagle J. H. Type D (Delta) hepatitis. JAMA 1989; 261:1321–1325.
5. Zuckerman A. J. Hepatitis E virus. BMJ 1990; 300:1475–1476.
6. Houghton M., Weiner A., Han J., et al. Molecular biology of the hepatitis C viruses: implications for diagnosis, development and control of viral disease. Hepatology 1991; 14:381–388.
7. Hoofnagle J. H., DiBisceglie A. M. Serologic diagnosis of acute and chronic viral hepatitis. Semin Liver Dis 1991; 11:73–83.
8. Miller R. H., Purcel R. H. Hepatitis C virus shares amino acid sequence similarity with pestiviruses and flaviviruses as well as membrane of two plant virus supergroups. Proc. Natl. Acad. Sci. USA 1990; 87:2057–2061.
9. Alter M. J., Hadler S. C., Judson F. N., et al. Risk factors for acute non-A, non-B hepatitis in the United States and association with hepatitis C virus infection. JAMA 1990; 264:2231–2235.

10. Saito I., Miyamura T., Ohbayashi A., et al. Hepatitis C virus infection is associated with the development of hepatocellular carcinoma. Proc. Natl. Acad. Sci. USA 1990; 87:6547–6549.
11. Hasan F., Jeffers L. J., Medina M. D., et al. Hepatitis C-associated hepatocellular carcinoma. Hepatology 1990; 12:589–591.
12. Houghton M., Choo O. L., Kuo G., et al. International patent application PCT/US90/02853. International Publication WO 90/14436.
13. Takamizawa A., Mori C., Fluke I., et al. Structure and organization of the hepatitis C virus genome isolated from human carriers. J. Virol. 1991; 65:1105–1113.
14. Choo Q. L., Richman K. H., Han J. H., et al. Genetic organization and diversity of the hepatitis C virus. Proc. Natl. Acad. Sci. USA 1991; 88:2451–2455.
15. Takeuchi K., Kubo Y., Boonmar S., et al. Nucleotide sequence of core and envelope genes of the hepatitis C virus genome derived directly from human healthy carriers. Nucleic Acids Research 1990; 18:4624.
16. Okamoto H., Okada S., Sugiyama Y., et al. The 5'-terminal sequence of the hepatitis C virus genome. Japan J. Exp. Med. 1990; 60:167–177.
17. Takeuchi K., Kubo Y., Boonmar S., et al. The putative nucleocapsid and envelope protein of the hepatitis C virus determined by comparison of the nucleotide sequences of two isolates derived from an experimentally infected chimpanzee and healthy human carriers. J. General Virology 1990; 71:3027–3033.
18. Houghton M., Choo Q. L., Kuo G. European Patent Application 88,310,922.5; Publication 318.216.
19. Kubo Y., Takeuchi K., Boonmar S., et al. A cDNA fragment of hepatitis C virus from an implicated donor of post-transfusion non-A non-B hepatitis in Japan. Nucleic Acids Research 1989; 17:10367–10372.
20. Enomoto N., Takada A., Nakao T., et al. There are two types of hepatitis C virus in Japan. Biochem. Biophys. Res. Com. 1990; 170:1021–1025.
21. Chen P. J., Lin M. H., Tu S. J., et al. Isolation of a complementary DNA fragment of hepatitis C virus in Taiwan revealed significant sequence variations compared with other isolates. Hepatology 1991; 14:73–78.
22. Ogata N., Alter H. J., Miller R. H., et al. Nucleotide sequence and mutation rate of the H strain of hepatitis C virus. Proc. Natl. Acad. Sci. USA. 1991; 88:3392–3396.
23. Kuo G., Choo Q. L., Alter H. J., et al. An assay for circulating antibodies to a major etiologic virus of human non-A, non-B hepatitis. Science 1989; 244:362–364.
24. Choo Q. L., Weiner A. J., Overby L. R., et al. Hepatitis C virus: the major causative agent of viral non-A, non-B hepatitis. Bri. Med. Bulletin. 1990; 46:423–441.
25. Shimizu Y. K., Weiner A. J., Rosenblatt J., et al. Early events in hepatitis C virus infection of chimpanzees. Proc. Natl. Acad. Aci. USA 1990; 87:6441–6444.
26. Harvey J. A., Purcell R. H., Shih J. W., et al. Detection of antibody to hepatitis C virus in prospectively followed transfusion recipients with acute and chronic non-A, non-B hepatitis. New Eng. J. Med. 1989; 321:1494–1500.
27. Poel C. L. V., Cuypers H. T. M., Reesink H. W., et al. Confirmation of hepatitis C virus infection by new antigen recombinant immunoblotting assays. Lancet 1991; 337:317–319.
28. Hosein B., Fang C. T., Popovsky M. A., et al. Improved serodiagnosis of hepatitis C virus infection with synthetic peptide antigen from capsid protein. Proc. Natl. Acad. Aci. USA 1991; 88:3647–3651.
29. Theilmann L., Blazek M., Goeser T., et al. False-positive anti-HCV tests in rheumatoid arthritis. Lancet 1990; 335:1346.
30. Eberling F., Nankkarineu R., Leikola J. Recombinant immunoblot assay for hepatitis C antibody as predictor of infectivity. Lancet 1990; 335:982–983.
31. Fong T.-L., DiBisceglie A. M., Waggoner J. G., et al. The significance of antibody to hepatitis C virus in patients with chronic hepatitis B. Hepatology 1991; 14:64–67.
32. Weiner A. J., Kuo G., Bradley D. W., et al. Detection of hepatitis C viral sequences in non-A, non-B hepatitis. Lancet 1990; 335:1–3.
33. Gason J. A., Tedder R. S., Briggs M., et al. Detection of hepatitis C viral sequences in blood donations by "nested" polymerase chain reaction and prediction of infectivity. Lancet 1990; 335:1419–1422.
34. Kaneko S., Unoura M., Kobayashi K., et al. Detection of serum hepatitis C virus RNA. Lancet 1990; 335:976.
35. Yoneyama T., Takeuchi K., Watanabe Y., et al. Detection of hepatitis C virus cDNA sequence by the polymerase chain reaction in hepatocellular carcinoma tissues. Jpn. J. Med. Sci. Biol. 1990; 43:89–94.
36. Kato N., Yokosuku O., Omata M., et al. Detection of hepatitis C virus ribonucleic acid in the serum by amplification with polymerase chain reaction. J. Clin. Invest. 1990; 86:1764–1767.
37. Okamoto H., Okada S. Sugiyama Y., et al. Detection of hepatitis C virus RNA by a two-stage polymerase chain reaction with two pairs of primers deduced from the 5'-non-coding region. Jpn. J. Exp. Med. 1990; 60:215–222.
38. Simmonds P., Zhang L. Q., Watson H. G., et al. Hepatitis C quantitation and sequencing in blood products, haemophiliacs and drug users. Lancet 1990; 336:1469–1472.
39. Kanai K., Iwata K., Nakao K., et al. Suppression of hepatitis C RNA by interferon-alfa. Lancet 1990; 336:245.
40. Christiano K., Di Bisceglie A. M., Hoofnagle J. H., et al. Hepatitis C viral RNA in serum of patients with chronic non-A, non-B hepatitis: Detection by the polymerase chain reaction using multiple primer sets. Hepatology 1991; 14:51–55.
41. Hu K. Q., Yu C. H., Villamil F. G., et al. Comparison of HCV cDNA polymerase chain reaction (PCR) using primers from the 5'non-coding and nonstructural regions of the HCV genome. Hepatology. (abstract) 1991; in press.
42. Innis M. A., Gelfand D. H., Sninsky J. H., et al. PCR Protocols: A Guide to Methods and Application. San Diego, Calif. Academic Press, Inc. 1990.
43. Smedile A., Bergmann K. F., Baroudy B. M., et al. Riboprobe assay for HDV RNA: a sensitive method for the detection of the HDV genome in clinical serum samples. J. Med. Virol. 1990; 30:20–24.
44. Hu K. Q., Yu C. H., Vierling J. M.. Detection of circulating HCV RNA by slot hybridization using a cDNA probe from the 5'-non-coding region. (abstract) Hepatology 1991; in press.
45. Chomczynski P., Sacchi N. Single-step method of RNA isolation by acid guanidinium thiocyanate-phenol-chloroform extract. Anal. Biochem. 1987; 162:156–159.
46. Molecular cloning, a laboratory manual. Sambrook J., Fritsch E. F., Maniatis T. eds. (second edition) Cold Spring Harbor Laboratory Press, 1989.
47. Alberti A. Diagnosis of hepatitis C. Facts and perspectives. J. Hepatol. 1991; 12:279–282.
48. Drmanac R., Strezosk Z., Labat I., et al. Reliable hybridization of oligonucleotides short as six nucleotides. DNA and Cell Biology 1990; 9:5527–5534.
49. Feinstone S. M., Alter J. H., Dienes H. P., et al. J Infect Dis 1981; 144:588–598.

50. Hu K.-Q., Vierling J. M. and Siddiqui A. Transactivation of HLA-DR gene by hepatitis B virus X gene product. Proc. Natl. Acad. Sci. (USA) 1990. 87:7140–7144.

We claim:

1. A method for detecting the presence of HCV in biological samples wherein said biological samples are selected from the group consisting of blood, blood components, secretions, cells other than tissue culture cells, sub-cellular components, and tissue biopsies from HCV infected patients and animals, and wherein said HCV is not amplified in vitro, said method comprising the steps of
   a) contacting said sample with multiple copies of a riboprobe which is fully complementary to at least six contiguous nucleotides of the 5'-non-coding region of the HCV genome;
   b) hybridizing said riboprobe to HCV RNA in said samples under conditions wherein said riboprobe hybridizes specifically to HCV and not to non-HCV nucleic acid; and
   c) detecting said hybridized riboprobe as an indication of the presence of HCV in said samples.

2. The method of claim 1 wherein said hybridizing is by a method selected from the group consisting of slot hybridization, dot blot hybridization, Northern hybridization and in situ hybridization.

3. The method of claim 1 wherein said riboprobe comprise nuleic acid which is fully complementary to at least 20 contiguous nucleotides within nueleotides 7–248 of the HCV.

4. The method of claim 3 wherein said hybridizing is by a method selected from the group consisting of slot hybridization, dot blot hybridization, Northern hybridization and in situ hybridization.

5. The method of claim 1 wherein said riboprobe comprises nucleic acid which is at least 90% complementary to 20 contiguous nucleotides in the 5'-non-coding region of the IIC-J1 strain of HCV.

6. The method of claim 5 wherein said hybridizing is by a method selected from the group consisting of slot hybridization, dot blot hybridization, Northern hybridization and in situ hybridization.

7. The method of claim 5 wherein said riboprobe comprises nucleic aid which is at least 95% complementary to 20 contiguous nucleotides in the 5'-non-coding region of the HC-J1 strain of HCV.

8. The method of claim 7 wherein said hybridizing is by a method selected from the group consisting of slot hybridization, dot blot hybridization Northern hybridization and in situ hybridization.

9. A method for detecting the presence of HCV in biological samples wherein said biological samples are selected from the group consisting of blood, blood components, secretions, cells other than tissue culture cells, sub-cellular components, and tissue biopsies from HCV infected patients and animals, and wherein said HCV is not amplified in vitro, said method comprising the steps of
   a) contacting said sample with multiple copies of a riboprobe which is fully complementary to at least 20 contiguous nucleotides of the HCV genome that are at least 90% conserved between HCV strains;
   b) hybridizing said riboprobe to HCV RNA in said samples under conditions wherein said riboprobe hybridizes specifically to HCV and not to non-HCV nucleic acid; and
   c) detecting said hybridized riboprobe as an indication of the presence of HCV in said samples.

10. The method of claim 9 wherein said hybridizing is by a method selected from the group consisting of slot hybridization, dot blot hybridization, Northern hybridization and in situ hybridization.

11. A kit for detecting the presence of HCV RNA in a biological sample wherein said biological sample is selected from the group consisting of blood, blood components, secretions, cells other than tissue culture cells, sub-cellular components, and tissue biopsies from HCV infected patients and animals, and wherein said HCV is not amplified in vitro, comprising
   (a) multiple copies of a riboprobe which is fully complementary to at least six contiguous nucleotides of the 5'-non-coding region of the HCV genome;

(b) apparatus for performing slot hybridization or dot blot hybridization on said biological sample with said riboprobe under conditions wherein said riboprobe hybridizes specifically to HCV and not to non-HCV nucleic acid; and (c) means for detecting the hybridization between the sample and the riboprobe.

12. The kit of claim 11 wherein the means for detecting the hybridization in step (c) is by providing the riboprobe in step (a) with label attached.

13. The kit of claim 12 wherein the label is selected from the group consisting of fluoresent markers, enzyme markers, and radioactivity.

14. The kit of claim 11 further comprising standard concentration samples of HCV RNA for quantification of said HCV RNA in said biological sample.

15. The kit of claim 11 wherein said riboprobe comprises nucleic acid which is fully complementary to at least 20 contiguous nucleotides within nucleotides 7–248 of the HCV genome.

16. The kit of claim 15 wherein the means for detecting the hybridization in step (c) is by providing the riboprobe in step (a) with label attached.

17. The kit of claim 16 wherein the label is selected from the group consisting of fluoresent markers, enzyme markers, and radioactivity.

18. The kit of claim 15 further comprising standard concentration samples of HCV RNA for quantification of said HCV RNA in said biological sample.

19. The kit of claim 11 wherein said riboprobe comprises nucleic acid which is at least 90% complementary to 20 contiguous nucleotides in the 540-non-coding region of the HC-J1 strain of HCV.

20. The kit of claim 19 wherein the means for detecting the hybridization in step (c) is by providing the riboprobe in step (a) with label attached.

21. The kit of claim 20 wherein the label is selected from the group consisting of fluoresent markers, enzyme markers, and radioactivity.

22. The kit of claim 19 further comprising standard concentration samples of HCV RNA for quantification of said HCV RNA in said biological sample.

23. The kit of claim 19 wherein said riboprobe comprises nucleic acid which is at least 95% complementary to 20 contiguous nucleotides in the 5'-non-coding region of the HC-J1 strain of HCV.

24. The kit of claim 23 wherein the means for detecting the hybridization in step (c) is by providing the riboprobe in step (a) with label attached.

25. The kit of claim 24 wherein the label is selected from the group consisting of fluorescent markers, enzyme markers, and radioactivity.

26. The kit of claim 23 further comprising standard concentration samples of HCV RNA for quantification of said HCV RNA in said biological sample.

27. A kit for detecting the presence of HCV RNA in a biological sample wherein said biological sample is selected from the group consisting of blood, blood components, secretions, cells other than tissue culture cells, sub-cellular components, and tissue biopsies from HCV infected patients and animals, and wherein said HCV is not amplified in vitro, comprising (a) multiple copies of a riboprobe which is fully complementary to at least 20 contiguous nucleotides of the HCV genome that are at least 90% conserved between HCV strains;

(b) apparatus for performing slot hybridization or dot blot hybridization on said biological sample with said riboprobe; and (c) means for detecting the hybridization between the sample and the riboprobe.

28. The kit of claim 27 wherein the means for detecting the hybridization in step (c) is by providing the riboprobe in step (a) with label attached.

29. The kit of claim 28 wherein the label is selected from the group consisting of fluoresent markers, enzyme markers, and radioactivity.

30. The kit of claim 27 further comprising standard concentration samples of HCV RNA for quantification of said HCV RNA in said biological sample.

31. A method for preparing blood free of HCV wherein said HCV is not amplified in vitro by screening samples of blood comprising (a) providing blood samples;

(b) providing multiple copies of a riboprobe which is fully complementary to at least six contiguous nucleotides of the 5'-non-coding region of the HCV genome;

(c) hybridizing the samples with said riboprobe under conditions wherein said riboprobe hybridizes specifically to HCV and not to non-HCV nucleic acid;

(d) detecting samples in which hybridization has occurred; and (e) removing the samples in which hybridization is detected.

32. The method of claim 31 wherein the hybridization is by a method selected from the group consisting of slot hybridization, dot blot hybridization, and Northern hybridization.

33. The method of claim 31 wherein the means for detecting in step (d) the hybridization in step (c) is by providing the riboprobe in step (a) with label attached.

34. The method of claim 33 wherein the label is selected from the group consisting of fluoresent markers, enzyme markers, and radioactivity.

35. The method of claim 31 wherein said riboprobe comprises nucleic acid which is fully complementary to at least 20 contiguous nucleotides within nucleotides 7–248 of the HCV genome.

36. The method of claim 35 wherein the hybridization is by a method selected from the group consisting of slot hybridization, dot blot hybridization, and Northern hybridization.

37. The method of claim 35 wherein the means for detecting in step (d) the hybridization in step (c) is by providing the riboprobe in step (a) with label attached.

38. The method of claim 37 wherein the label is selected from the group consisting of fluoresent markers, enzyme markers, and radioactivity.

39. The method of claim 31 wherein said riboprobe comprises nucleic acid which is at least 90% complementary to 20 contiguous nucleotides in the 5'-non-coding region of the HC-J1 strain of HCV.

40. The method of claim 39 wherein the hybridization is by a method selected from the group consisting of slot hybridization, dot blot hybridization, and Northern hybridization.

41. The method of claim 39 wherein the means for detecting in step (d) the hybridization in step (c) is by providing the riboprobe in step (a) with label attached.

42. The method of claim 41 wherein the label is selected from the group consisting of fluoresent markers, enzyme markers, and radioactivity.

43. The method of claim 39 wherein said riboprobe comprises nucleic acid which is at least 95% complementary to 20 nucleotides in the 5'-non-coding region of the HC-J1 strain of HCV.

44. The method of claim 43 wherein the hybridization is by a method selected from the group consisting of slot hybridization, dot blot hybridization, and Northern hybridization.

45. The method of claim 43 wherein the means for detecting in step (d) the hybridization in step (c) is by providing the riboprobe in step (a) with label attached.

46. The method of claim 45 wherein the label is selected from the group consisting of fluoresent markers, enzyme markers, and radioactivity.

47. A method for preparing blood free of HCV by screening samples of blood wherein said HCV is not amplified in vitro comprising (a) providing blood samples;

(b) providing multiple copies of a riboprobe which is fully complementary to at least 20 contiguous nucleotides of the HCV genome that are at least 90% conserved between HCV strains;

(c) hybridizing the samples with said riboprobe;

(d) detecting samples in which hybridization has occurred; and (e) removing the samples in which hybridization is detected.

48. The method of claim 47 wherein the hybridization is by a method selected from the group consisting of slot hybridization, dot blot hybridization, and Northern hybridization.

49. The method of claim 47 wherein the means for detecting in step (d) the hybridization in step (c) is by providing the riboprobe in step (a) with label attached.

50. The kit of claim 49 wherein the label is selected from the group consisting of fluoresent markers, enzyme markers, and radioactivity.

51. A method for diagnosis of HCV infection wherein said HCV is not amplified in vitro comprising (a) providing biological samples wherein said biological samples are selected from the group consisting of blood, blood components, secretions, cells other than tissue culture cells, sub-cellular components, and tissue biopsies from HCV infected patients and animals;

(b) providing multiple copies of a riboprobe which is fully complementary to at least six contiguous nucleotides of the 5'-non-coding region of the HCV genome;

(c) hybridizing said samples with said probe under conditions wherein said probe hybridizes specifically to HCV and not to non-HCV nucleic acid;

(d) detecting samples in which hybridization has occurred as an indication of the presence of HCV in said samples; and (e) diagnosing HCV infection in said patients or animals by the presence of HCV in said sample.

52. The method of claim 51 wherein the hybridization of step (c) is by a method selected from the group consisting of slot hybridization, dot blot hybridization, and Northern hybridization.

53. The method of claim 51 wherein the means in step (d) for detecting the hybridization in step (c) is by providing the riboprobe in step (b) with label attached.

54. The method of claim 53 wherein the label is selected from the group consisting of fluoresent markers, enzyme markers, and radioactivity.

55. The method of claim 51 wherein said riboprobe comprises nucleic acid which is fully complementary to at least 20 contiguous nucleotides within nucleotides 7–248 of the HCV genone.

56. The method of claim 55 wherein the hybridization of step (c) is by a method selected from the group consisting of slot hybridization, dot blot hybridization, and Northern hybridization.

57. The method of claim 55 wherein the means in step (d) for detecting the hybridization in step (c) is by providing the riboprobe in step (b) with label attached.

58. The method of claim 57 wherein the label is selected from the group consisting of fluoresent markers, enzyme markers, and radioactivity.

59. The method of claim 51 wherein said riboprobe comprises nucleic acid which is at least 90% complementary to 20 contiguous nucleotides in the 5'-non-coding region of the HC-J1 strain of HCV.

60. The method of claim 59 wherein the hybridization of step (c) is by a method selected from the group consisting of slot hybridization, dot blot hybridization, and Northern hybridization.

61. The method of claim 59 wherein the means in step (d) for detecting the hybridization in step (c) is by providing the riboprobe in step (b) with label attached.

62. The method of claim 61 wherein the label is selected from the group consisting of fluoresent markers, enzyme markers, and radioactivity.

63. The method of claim 59 wherein said riboprobe comprises nucleic acid which is at least 95% complementary to 20 contiguous nucleotides in the 5'-non-coding region of the HC-J1 strain of HCV.

64. The method of claim 63 wherein the hybridization of step (c) is by a method selected from the group consisting of slot hybridization, dot blot hybridization, and Northern hybridization.

65. The method of claim 63 wherein the means in step (d) for detecting the hybridization in step (e) is by providing the riboprobe in step (b) with label attached.

66. The method of claim 65 wherein the label is selected from the group consisting of fluoresent markers, enzyme markers, and radioactivity.

67. A method for monitoring anti-HCV therapy by detecting the presence and relative quantity of HCV in biological samples at a variety of time points wherein said biological samples are selected from the group consisting of blood, blood components, secretions, cells other than tissue culture cells, sub-cellular components, and tissue biopsies from HCV infected patients and animals, and wherein said HCV is not amplified in vitro, comprising (a) providing said biological samples at various points before, during and after administration of said therapy;

(b) providing multiple copies of a riboprobe which is fully complementary to at least six contiguous nucleotides of the 5'non-coding region of the HCV genome;

(c) hybridizing said samples with said probe;

(d) detecting samples in which hybridization has occurred;

(e) quantifying the amount of HCV RNA present in each sample where hybridization is detected; and (f) comparing the results of step (e) from any at least two samples taken at different points before, during or after administration of said therapy.

68. The method of claim 67 wherein the hybridization of step (c) is by a method selected from the group consisting of slot hybridization, dot blot lybridization, and Northern hybridization.

69. The method of claim 67 wherein the means in step (d) for detecting the hybridization in stop (c) is by providing the riboprobe in stop (b) with label attached.

70. The method of claim 69 wherein the label is selected from the group consisting of fluoresent markers, enzyme markers, and radioactivity.

71. The method claim 67 wherein said riboprobe comprises nucleic acid which is fully complementary to at least 20 contiguous nucleotides within nucleotides 7–248 of the HCV genome.

72. The method of claim 71 wherein the hybridization of step (c) is by a method selected from the group consisting of slot hybridization, dot blot hybridization, and Northern hybridization.

73. The method of claim 71 wherein the means in step (d) for detecting the hybridization in step (c) is by providing the riboprobe in step (b) with label attached.

74. The method claim 73 wherein the label is selected from the group consisting of fluoresent markers, enzyme markers, and radioactivity.

75. The method of claim 71 wherein quantifying is done by comparing the amount hybridization in said sample to the amount or hybridization in standard solutions containing known quantities of HCV RNA.

76. The method of claim 61 wherein said riboprobe comprises nucleic acid sequence which is at least 90% complementary to 20 nucleotides in the 5'-non-coding region of the HC-J1 strain of HCV.

77. The method of claim 76 wherein the hybridization of step (c) is by a method selected from the group consisting of slot hybridization, dot blot hybridization, and Northern hybridization.

78. The method of claim 76 wherein the means in step (d) for detecting the hybridization in step (c) is by providing the riboprobe in step (b) with label attached.

79. The method of claim 78 wherein the label is selected from the group consisting of fluoresent markers, enzyme markers, and radioactivity.

80. The method of claim 76 wherein quantifying is done by comparing the amount of hybridization in said sample to the amount of hybridization in standard solutions containing known quantities of HCV RNA.

81. The method of claim 76 wherein said riboprobe comprises nucleic acid which at least 95% complementary to 20nucleotides in the 5'-non-coding region of the HC-J1 strain of HCV.

82. The method of claim 81 wherein the hybridization or step (c) is by a method selected from the group consisting of slot hybridization, dot blot hybridization, and Northern hybridization.

83. The method of claim 81 wherein the means in step (d) for detecting the hybridization in step (c) is by providing the riboprobe in step (b) with label attached.

84. The method of claim 83 wherein the label is selected from the group consisting of fluoresent markers, enzyme markers, and radioactivity.

85. The method of claim 81 wherein quantifying is done by comparing the amount of hybridization in said sample to the amount of hybridization in standard solutions containing known quantities of HCV RNA.

86. A method for monitoring anti-HCV therapy by detecting the presence and relative quantity of HCV in biological samples at a variety of time points wherein said biological samples are selected from the group consisting of blood, blood components, secretions, cells other than tissue culture cells, sub-cellular components, and tissue biopsies from HCV infected patients and animals, and wherein said HCV is not amplified in vitro, comprising (a) providing said biological samples at various points before, during and after administration of said therapy;

(b) providing multiple copies of a riboprobe which is fully complementary to at least 20 contiguous nucleotides of the HCV genome that are at least 90% conserved between HCV strains;

(c) hybridizing said samples with said probe;

(d) detecting samples in which hybridization has occurred;

(e) quantifying the amount of HCV RNA present in each sample where hybridization is detected; and (f) comparing the results of step (e) from any at least two samples taken at different points before, during or after administration of said therapy.

87. The method of claim 86 wherein the hybridization of step (c) is by a method selected from the group consisting of slot hybridization, dot blot hybridization, and Northern hybridization.

88. The method of claim 86 wherein the means in step (d) for detecting the hybridization in step (c) is by providing the riboprobe in step (b) with label attached.

89. The method of claim 88 wherein the label is selected from the group consisting of fluoresent markers, enzyme markers, and radioactivity.

90. The method of claim 86 wherein quantifying is done by comparing the amount of hybridization in said sample to the amount of hybridization in standard solutions containing known quantities of HCV RNA.

91. The method of claim 86 used to design an anti-HCV therapy further comprising the step of determining from the results of step (e) how much and when to deliver said anti-HCV therapy in order to lower the amount of HCV present in the biological samples being monitored.

92. A method for diagnosis of HCV infection wherein said HCV is not amplified in vitro comprising (a) providing biological samples wherein said biological samples are selected from the group consisting of blood, blood components, secretions, cells other than tissue culture cells, sub-cellular components and tissue biopsies from HCV infected patients and animals;

(b) providing multiple copies of a riboprobe which is fully complementary to at least 20 contiguous nucleotides of the HCV genome that are at least 90% conserved between HCV strains;

(c) hybridizing said samples with said probe under conditions wherein said probe hybridizes specifically to HCV and not to non-HCV nucleic acid;

(d) detecting samples in which hybridization has occurred as an indication of the presence of HCV in said samples; and (e) diagnosing HCV infection in said patients or animals by the presence of HCV in said sample.

93. The method of claim 92 wherein the hybridization of step (c) is by a method selected front the group consisting of slot hybridization, dot blot hybridization, and Northern hybridization.

94. The method of claim 92 wherein the means in step (d) for detecting the hybridization in step (c) is by providing the riboprobe in step (b) with label attached.

95. The method of claim 92 wherein the label is selected from the group consisting of fluoresent markers, enzyme markers, and radioactivity.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 242 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:1:

```
ACTCCACCAT AGATCACTCC CCTGTGAGGA ACTACTGTCT TCACGCAGAA AGCGTCTAGC      60

CATGGCGTTA GTTAGAGTGT CGTGCAGCCT CCAGGACCCC CCCTCCCGGG AGAGCCATAG     120

TGGTCTGCGG AACCGGTGAG TACACCGGAA TTGCCAGGAC GACCGGGTCC TTTCTTGGAT     180

AAACCCGCTC AATGCCTGGA GATTTGGGCG CGCCCCCGCA AGACTGCTAG CCGAGTAGTG     240

TT                                                                    242
```